US008632477B2

(12) United States Patent  
Munehiro

(10) Patent No.: US 8,632,477 B2  
(45) Date of Patent: Jan. 21, 2014

(54) METHOD FOR DETERMINING POSITION OF LOWER JAW, APPARATUS AND PROGRAM THEREOF

(76) Inventor: Motonori Munehiro, Hiroshima (JP)

( * ) Notice: Subject to any disclaimer, the term of this patent is extended or adjusted under 35 U.S.C. 154(b) by 593 days.

(21) Appl. No.: 12/687,867

(22) Filed: Jan. 14, 2010

(65) Prior Publication Data

US 2010/0151409 A1  Jun. 17, 2010

Related U.S. Application Data

(63) Continuation of application No. PCT/JP2008/062723, filed on Jul. 14, 2008.

(30) Foreign Application Priority Data

Jul. 17, 2007 (JP) ................................ 2007-186091

(51) Int. Cl.
*A61B 5/103* (2006.01)
*A61B 5/117* (2006.01)

(52) U.S. Cl.
USPC .......................................................... 600/590

(58) Field of Classification Search
USPC ............................. 600/587, 590, 595; 702/19
See application file for complete search history.

(56) References Cited

U.S. PATENT DOCUMENTS

| 3,160,955 | A |   | 12/1964 | De Pietro et al. |
| 3,390,459 | A | * | 7/1968  | Seidenberg ...................... 433/27 |
| 4,303,077 | A | * | 12/1981 | Lewin et al. ...................... 433/69 |
| 5,154,608 | A |   | 10/1992 | Feher |
| 5,871,352 | A |   | 2/1999  | Kawai et al. |
| 5,905,658 | A |   | 5/1999  | Baba |
| 6,120,290 | A | * | 9/2000  | Fukushima et al. ............ 433/69 |

FOREIGN PATENT DOCUMENTS

| JP | 48-10870 B1 | 4/1973 |
| JP | 50-7754 Y2  | 3/1975 |
| JP | 6-269468 A  | 9/1994 |
| JP | 9-42923 A   | 2/1997 |
| JP | 9-238963 A  | 9/1997 |
| JP | H9-322883 A | 12/1997 |

(Continued)

OTHER PUBLICATIONS

International Search Report (ISR) issued in PCT/JP2008/062723 (parent application).

(Continued)

*Primary Examiner* — Max Hindenburg  
*Assistant Examiner* — Jonathan M Foreman

(57) ABSTRACT

A normal lower jaw position of an examinee is determined. A lower jaw position determining method for determining a normal lower jaw position of an examinee, includes: center calculating for obtaining measurement data by measuring movement of a head of the examinee, and calculating a center of movement resulting from approximating the movement of the head as rotational movement of a rigid body; lower jaw orbit measuring for measuring a plurality of orbits of masticatory movement of the lower jaw, for a plurality of lower jaw positions of the examinee; and position determining for (i) approximating the masticatory movement of the lower jaw as rotational movement of a rigid body to find one of the plurality of measured orbits of the lower jaw whose center of movement in the approximation matches the calculated center of movement of the head, (ii) determining a lower jaw position that corresponds to the found orbit of the lower jaw to be a normal lower jaw position for the examinee, and (iii) outputting the determined normal lower jaw position.

16 Claims, 17 Drawing Sheets

(56) References Cited

FOREIGN PATENT DOCUMENTS

| JP | 2002-336282 A | 11/2002 |
|---|---|---|
| JP | 2002-355264 A | 12/2002 |
| JP | 2004-167032 A | 6/2004 |
| JP | 2006-239104 A | 9/2006 |

OTHER PUBLICATIONS

Written Opinion (PCT/ISA/237) issued in PCT/JP2008/062723 (parent application).

Kapandji, "The Physiology of the Joints", The Trunk and the Vertebral Column, Churchill Livingstone, Edinburgh, London and New York, 1974, vol. 3, pp. 174-175, 180-184, 185, 216-217, 236-237 and 248-249.

Guzay, "Efficiency in Occlusal Function", Basal Facts, The International Journal of Biologic Stress & Disease, vol. 7, No. 3, pp. 228-246.

Guzay, "Quadrant theorem-part two", Basal Facts, Spring 1977, vol. 2, No. 1, pp. 19-33.

Guzay, "Introduction to the quadrant theorem", Basal Facts, Winter 1976, vol. 1, No. 4, pp. 153-160.

Guzay, "Quadrant theorem Part III", Basal Facts, 1977 • 78, vol. 2, No. 4, pp. 171-183.

\* cited by examiner

104

EXAMINEE ID12345

HEAD MOVEMENT CENTER(X,Y,Z)=(10,10,213)

| LOWER JAW POSITION | | ORBIT | | SPEED DIRECTION | |
|---|---|---|---|---|---|
| LEFT AND RIGHT | FORWARD AND BACKWARD | FRONT | SIDE | α | β |
| 0 | 0 | } | ⁄ | 3 | 22 |
| 0 | 1 | \| | ⁄ | 0 | 20 |
| 0 | -1 | \ | ~ | -5 | 16 |
| *** | *** | *** | *** | *** | *** |

FIG.8

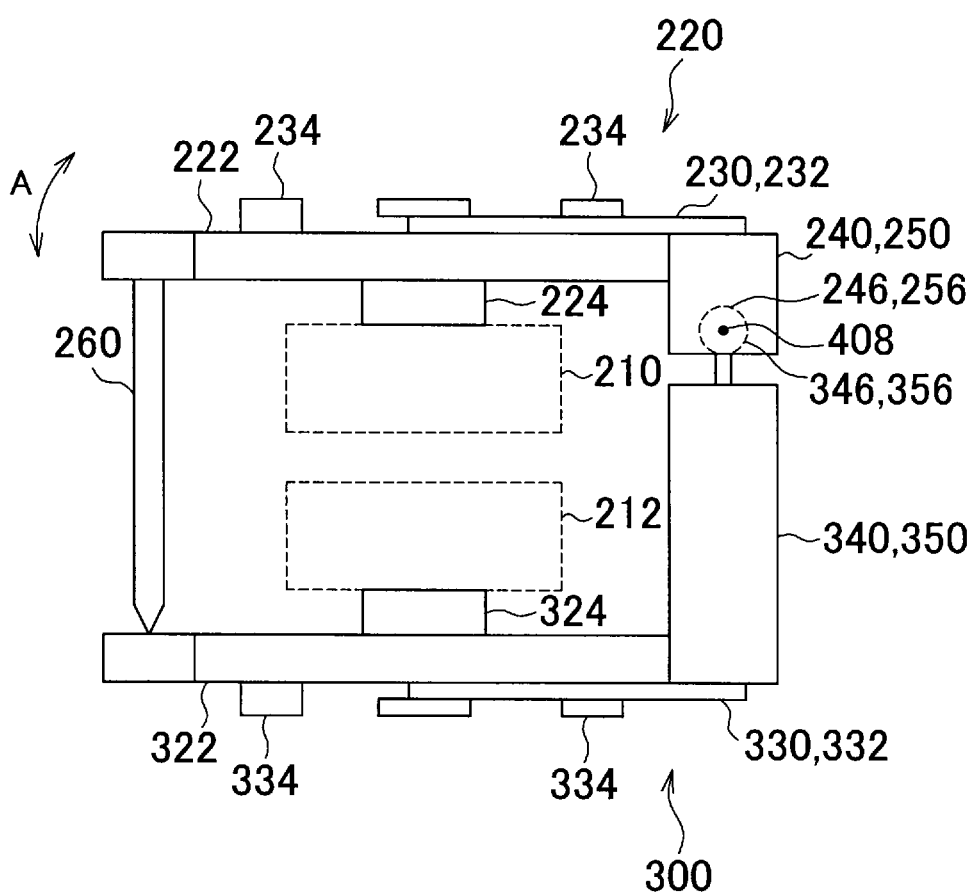
F I G . 13

METHOD FOR DETERMINING POSITION OF LOWER JAW, APPARATUS AND PROGRAM THEREOF

CROSS REFERENCE TO RELATED APPLICATION

This is a continuation application of PCT/JP2008/062723 filed on Jul. 14, 2008 which claims priority from a Japanese Patent Application No. 2007-186091 filed on Jul. 17, 2007, the contents of which are incorporated herein by reference.

BACKGROUND

1. Technical Field

The present invention relates to a method, an apparatus, and a program for determining a position of a lower jaw. In particular, the present invention relates to a method, an apparatus, and a program for determining a position of a lower jaw, by which a normal position of a lower jaw of an examinee can be determined.

2. Related Art

There has already been an analysis apparatus for obtaining a contact pressure distribution of a jaw joint in a particular lower jaw position (refer to Japanese Patent Application Publication No. H9-322883 for example). This analysis apparatus obtains a contact pressure distribution of a jaw joint by reading an X-ray photograph of the jaw joint, and using the lower jawbone and the skull in the read jaw joint as a rigid body model thereby computationally adding an imaginary binding strength to exclude any contradicting force.

However, the mentioned analysis apparatus, although capable of obtaining a contact pressure distribution of a jaw joint in a certain lower jaw position, it is not possible to know whether the lower jaw position is a normal lower jaw position for the examinee. Moreover, it is burdensome to take in the X-ray photograph of the jaw joint or to repeat a calculation loop by setting a virtual binding strength until the calculation converges.

SUMMARY

In view of the above, according to an aspect of the innovations herein, provided are a lower jaw position determining method, a lower jaw position determining apparatus, a program and an articulator, which are capable of solving the above-stated problems. This object is achieved by combinations of features described in the independent claims. The dependent claims define further advantageous and concrete examples of the present invention.

According to a first aspect of the innovations herein, provided is a lower jaw position determining method for determining a normal lower jaw position of an examinee, including: center calculating for obtaining measurement data by measuring movement of a head of the examinee, and calculating a center of movement resulting from approximating the movement of the head as rotational movement of a rigid body; lower jaw path measuring for measuring a plurality of paths of masticatory movement of the lower jaw, for a plurality of lower jaw positions of the examinee; and position determining for (i) approximating the masticatory movement of the lower jaw as rotational movement of a rigid body to find one of the plurality of measured paths of the lower jaw whose center of movement in the approximation matches the calculated center of movement of the head, (ii) determining a lower jaw position that corresponds to the found path of the lower jaw to be a normal lower jaw position for the examinee, and (iii) outputting the determined normal lower jaw position.

According to a second aspect of the innovations herein, provided is a lower jaw position determining apparatus for determining a normal lower jaw position of an examinee, including: a center calculating section for obtaining measurement data by measuring movement of a head of the examinee, and calculating a center of movement resulting from approximating the movement of the head as rotational movement of a rigid body; a lower jaw path measuring section for measuring a plurality of paths of masticatory movement of the lower jaw, for a plurality of lower jaw positions of the examinee; and a position determining section for (i) approximating the masticatory movement of the lower jaw as rotational movement of a rigid body to find one of the plurality of measured paths of the lower jaw whose center of movement in the approximation matches the calculated center of movement of the head, (ii) determining a lower jaw position that corresponds to the found path of the lower jaw to be a normal lower jaw position for the examinee, and (iii) outputting the determined normal lower jaw position.

According to a third aspect of the innovations herein, provided is a program for controlling a lower jaw position determining apparatus for determining a normal lower jaw position of an examinee, the program causing the lower jaw position determining apparatus to execute: center calculating for obtaining measurement data by measuring movement of a head of the examinee, and calculating a center of movement resulting from approximating the movement of the head as rotational movement of a rigid body; lower jaw path measuring for measuring a plurality of paths of masticatory movement of the lower jaw, for a plurality of lower jaw positions of the examinee; and position determining for (i) approximating the masticatory movement of the lower jaw as rotational movement of a rigid body to find one of the plurality of measured paths of the lower jaw whose center of movement in the approximation matches the calculated center of movement of the head, (ii) determining a lower jaw position that corresponds to the found path of the lower jaw to be a normal lower jaw position for the examinee, and (iii) outputting the determined normal lower jaw position.

According to a fourth aspect of the innovations herein, provided is an articulator including: an upper arch portion to which a denture mold model for an upper jaw is attached; and a lower arch portion to which a denture mold model for a lower jaw is attached, the lower arch portion rotatably linked to the upper arch portion via a pair of spherical bearings, where a distance between the pair of spherical bearings is variable.

The summary of the invention does not necessarily describe all necessary features of the present invention. The present invention may also be a sub-combination of the features described above.

BRIEF DESCRIPTION OF THE DRAWINGS

FIG. 8 shows an example of information stored in a lower jaw position storage 104.

FIG. 13 is a side view of an example of an articulator 200 used in Step S270 and Step S280 in FIG. 10.

Figure 1:
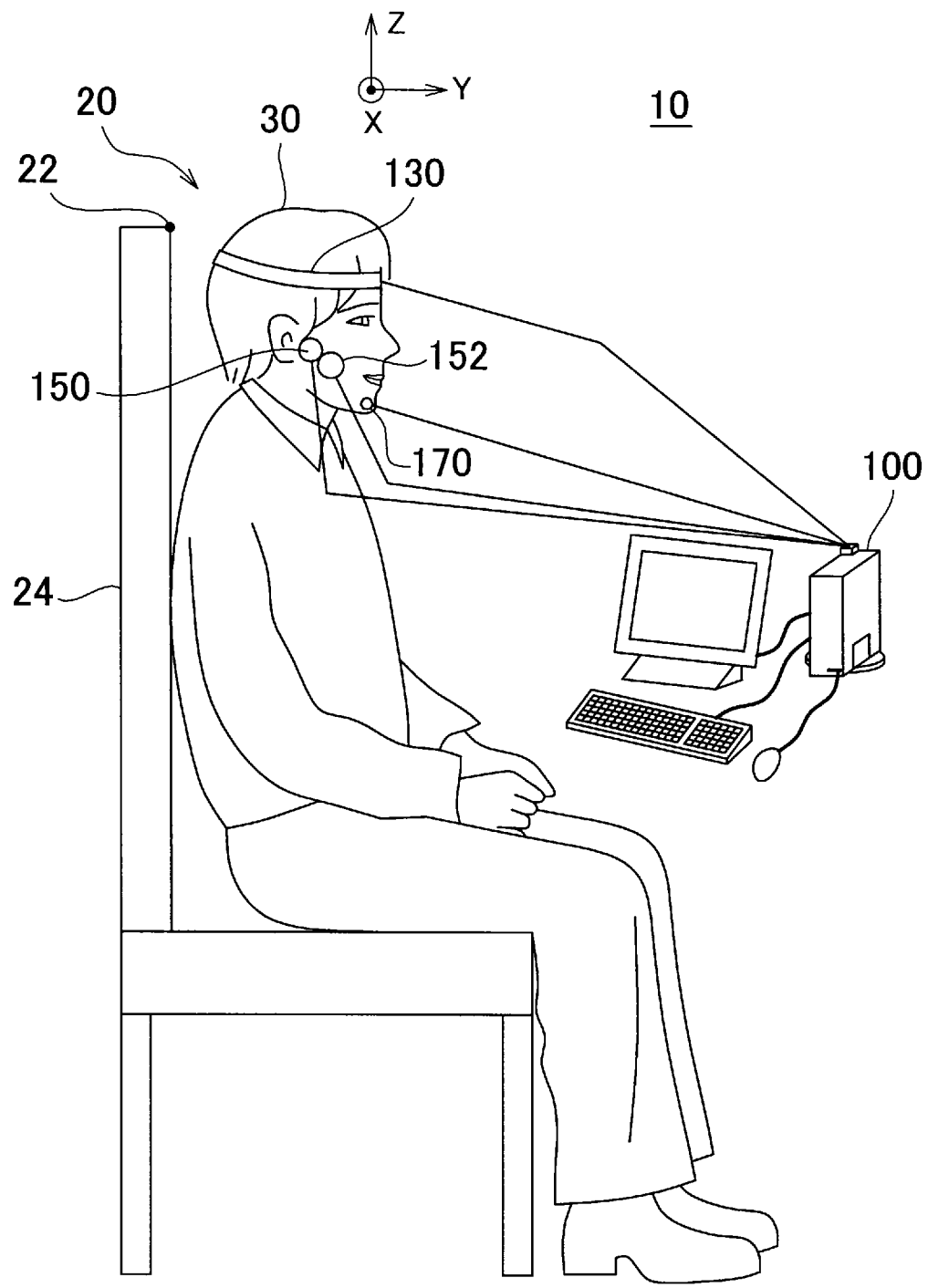
FIG. 1 is a schematic view of a lower jaw position determining system 10.

EXPLANATION OF REFERENCE NUMERALS 10 lower jaw position determining system, 20 examinee, 22 reference position, 24 chair, 30 head, 32 center of movement, 34 spinal cord, 33 head barycenter, 36 skull, 38 atlas, 39 axis, 40 lower jaw, 44 occluding plane, 45 reference plane, 47 straight line, 50 load, 51 load, 52 load, 53 drag, 54 load, 55 spherical surface, 56 curved surface, 100 lower jaw position determining apparatus, 102 recording medium, 104 lower jaw position storage, 110 center calculating section, 120 occluding plane setting section, 130 head movement measuring section, 140 masseter relaxing section, 150 electrode pad, 152 electromyograph, 160 lower jaw path measuring section, 162 sensor unit, 170 sensor, 172 sensor body, 176 engaging section, 180 attachment tool, 182 tool body, 184 engaging section, 186 elongating section, 190 position determining section, 192 speed calculating section, 194 speed determining section, 200 articulator, 210 upper denture mold model, 212 lower denture mold model, 220 upper arch portion, 222 upper arch body, 224 model attaching section, 226 link pin, 228 groove, 230 link member, 232 link member, 234 leg, 236 arm, 240 connector, 242 concave portion, 244 link pin, 246 spherical bearing, 250 connector, 252 concave portion, 254 link pin, 256 spherical bearing, 260 incisal pin, 300 lower arch portion, 322 lower arch body, 324 model attaching section, 326 link pin, 328 groove, 330 link member, 332 link member, 334 leg, 336 arm, 340 upright portion, 342 concave portion, 344 link pin, 346 sphere, 350 upright portion, 352 concave portion, 354 link pin, 356 sphere, 400 pedestal, 402 reference bottom surface, 404 reference anterior surface, 406 up-and-down section, 408 condyle position.

DESCRIPTION OF EXEMPLARY EMBODIMENTS

The invention will now be described based on the preferred embodiments, which do not intend to limit the scope of the present invention, but exemplify the invention. All of the features and the combinations thereof described in the embodiment are not necessarily essential to the invention.

Although some aspects of the present invention have been described by way of exemplary embodiments, it should be understood that those skilled in the art might make many changes and substitutions without departing from the spirit and the scope of the present invention which is defined only by the appended claims.

FIG. 1 is a schematic view of a lower jaw position determining system 10. The lower jaw position determining system 10 includes a lower jaw position determining apparatus 100, a head movement measuring section 130, an electrode pad 150, and a sensor 170, and determines a normal lower jaw position for an examinee 20. The head movement measuring section 130 includes a magnetic sensor fixed to a head 30 of the examinee 20, and measures, using this magnetic sensor, the movement of the head 30, and passes the measured data to the lower jaw position determining apparatus 100. The electrode pad 150 is attached to both the left and right lower jaw notches as well as the culmination of the back of the cervix of the examinee 20. An electromyograph 152 attached to the masseter and temporalis is electrically connected to the later detailed masseter relaxing section 140. The sensor 170 is a magnetic sensor attached to the lower jaw 40 of the examinee 20. Here, a reference position 22 is set to a chair 24, and the shoulders and the head 30 of the examinee 20 are respectively fixed to the chair 24.

Figure 2:
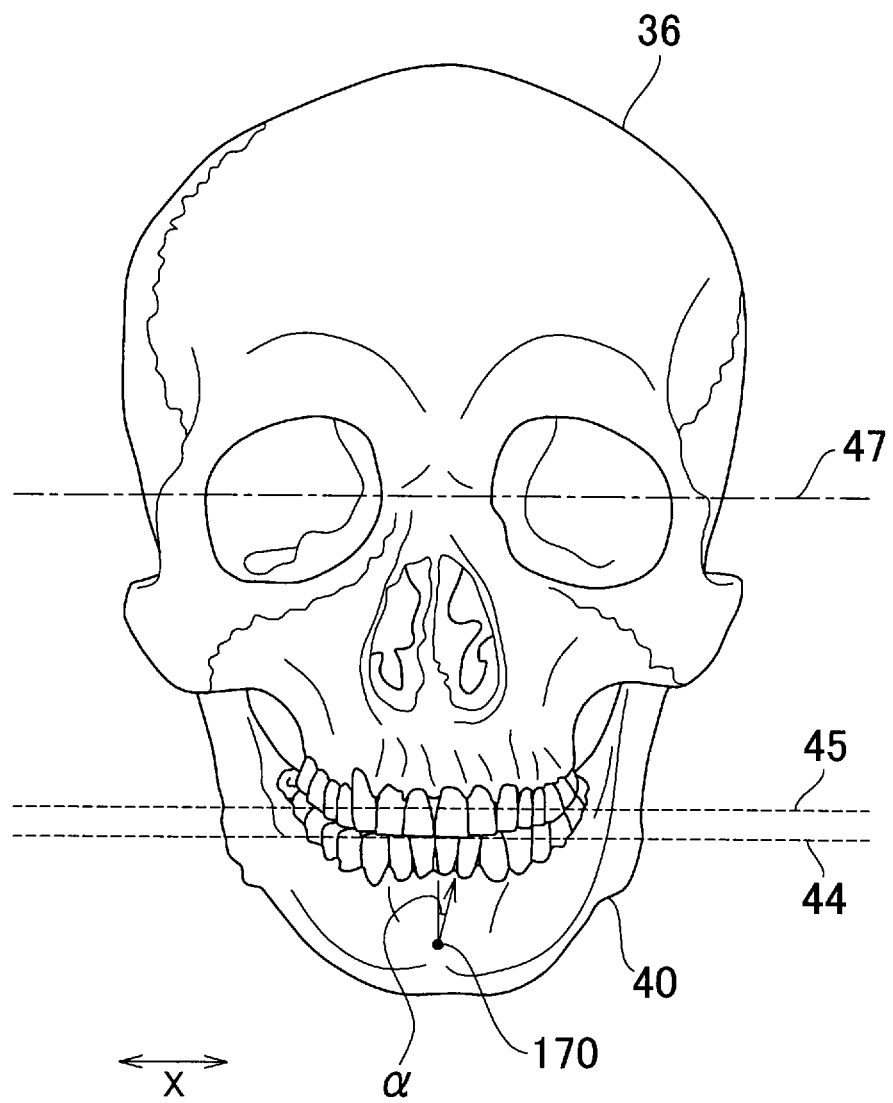
FIG. 2 is a front view of a skull 36 and a lower jaw 40 drawn to explain the lower jaw position.
Figure 3:
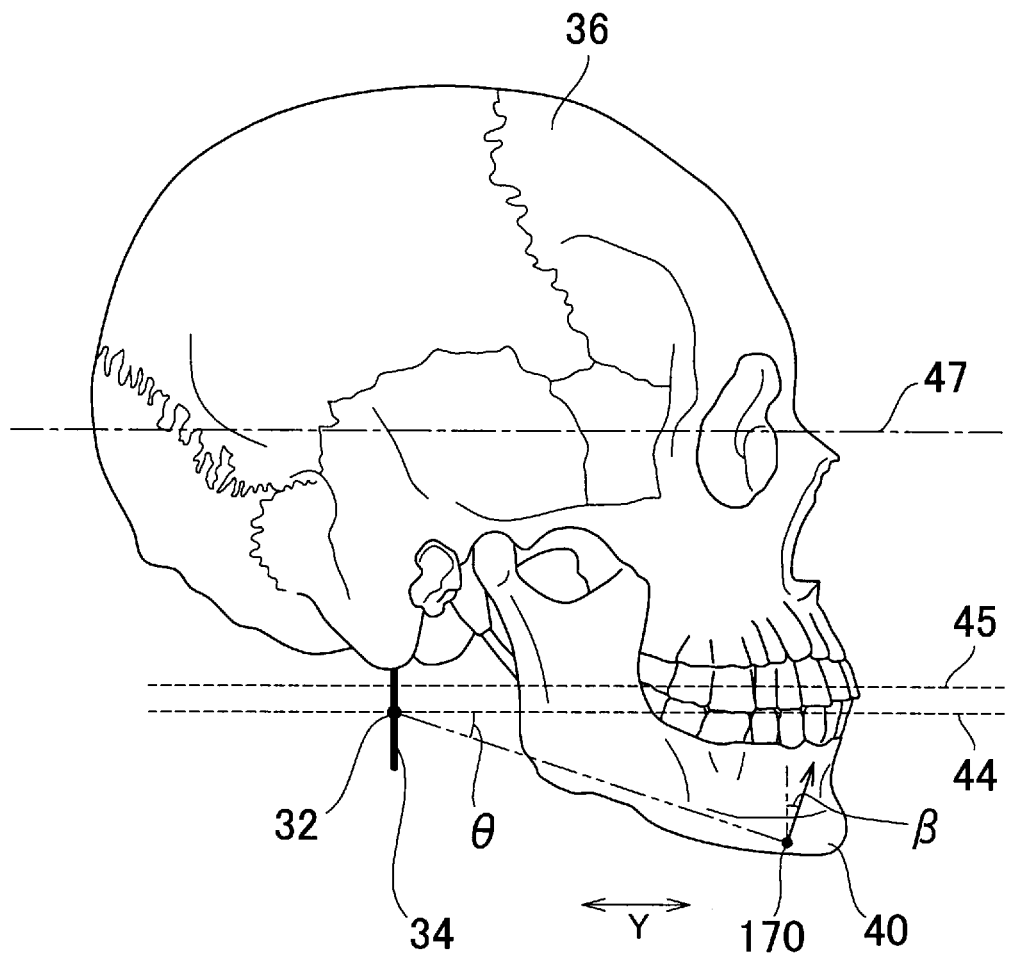
FIG. 3 is a side view of the skull 36 and the lower jaw 40.
Figure 4:
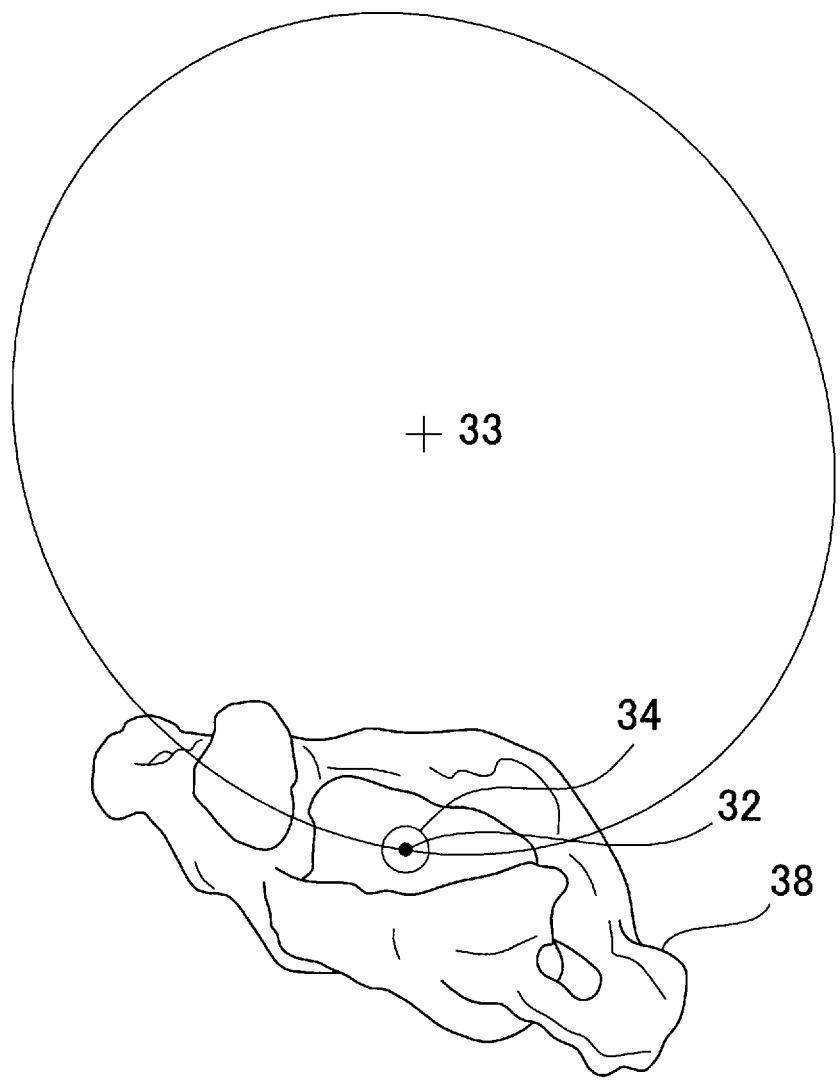
FIG. 4 is a perspective view of an atlas 38.
Figure 5:
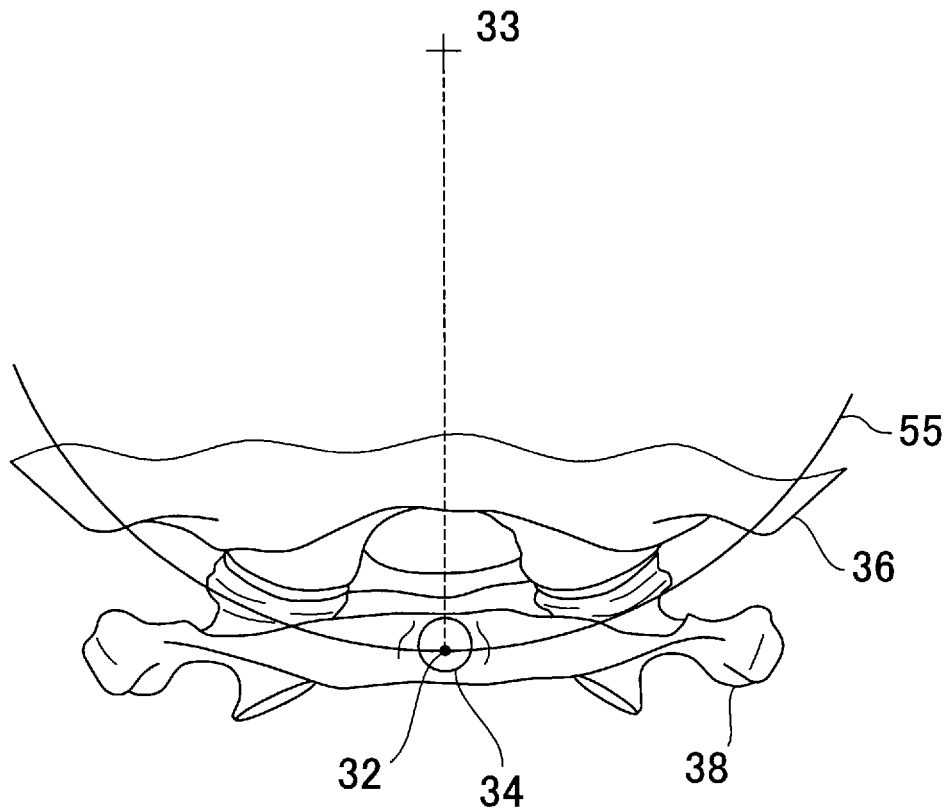
FIG. 5 is a side view of the atlas 38.
Figure 6:
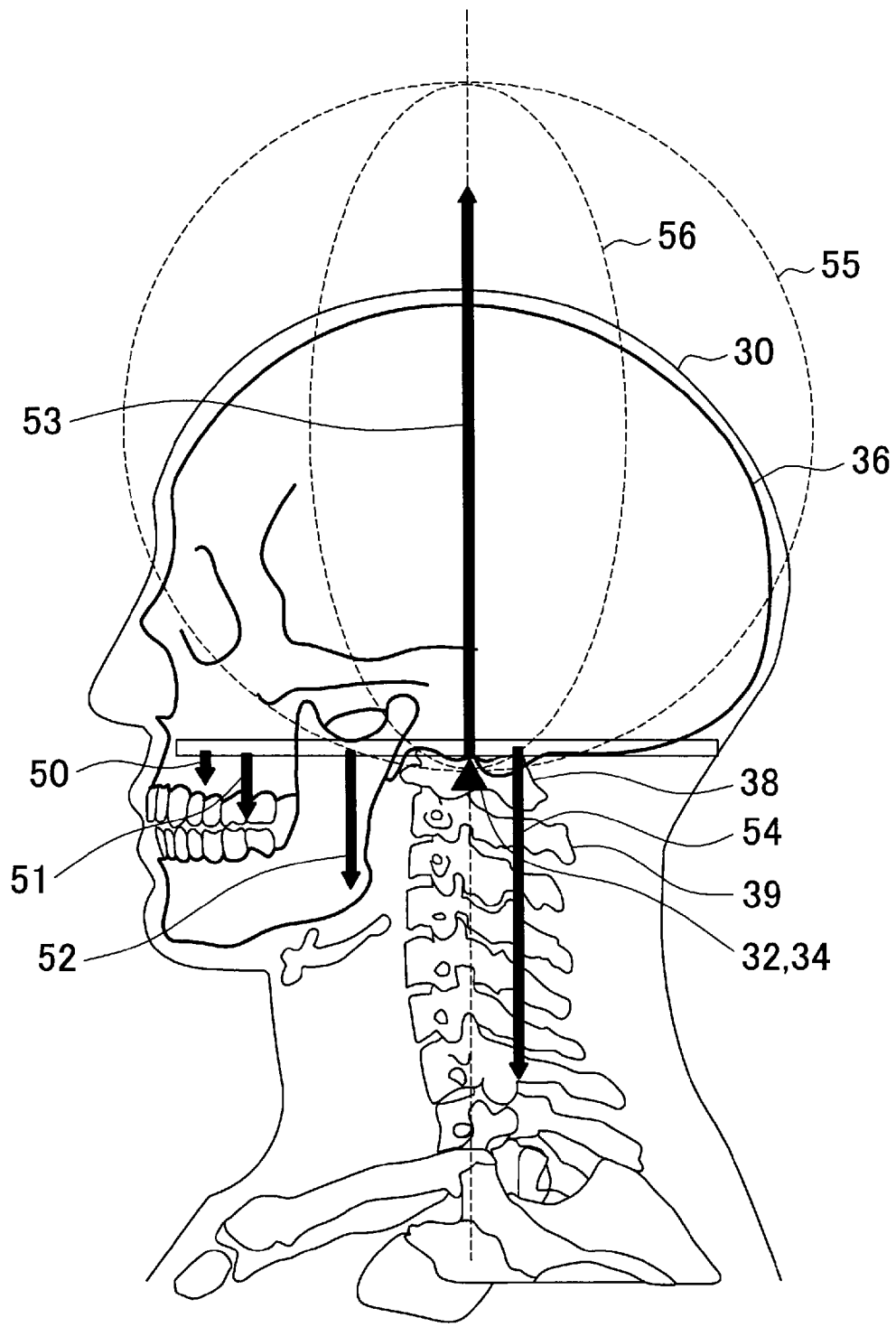
FIG. 6 is a side view of the skull 36, exhibiting a mechanical balance in which the skull 36 is supported in a resting state.

FIG. 2 is a front view of the skull 36 and the lower jaw 40 drawn to explain the lower jaw position, and FIG. 3 is a side view of the skull 36 and the lower jaw 40. Further, FIG. 4 and FIG. 5 are respectively side and perspective views of an atlas 38. FIG. 6 is a side view of the skull 36, exhibiting a mechanical balance in which the skull 36 is supported in a resting state.

In FIG. 2 and FIG. 3, an occluding plane 44 is at the distal end of the lower jaw 40 with respect to the skull 36 in masticatory movement. The lower jaw position determining system 10 aims to determine a normal occluding plane 44 as well as a lower jaw position in the normal occluding plane 44 more accurately than conventionally. While pursuing this, the present embodiment determines a normal lower jaw position, based on the findings, as shown in FIG. 2 and FIG. 6, that the head 30 moves with the spinal cord 34 as the center of movement 32, and that the masticatory movement as external force to the skull 36, the atlas 38, and the axis 39 is also preferably performed with the spinal cord 34 as the center of the movement 32.

Figure 7:
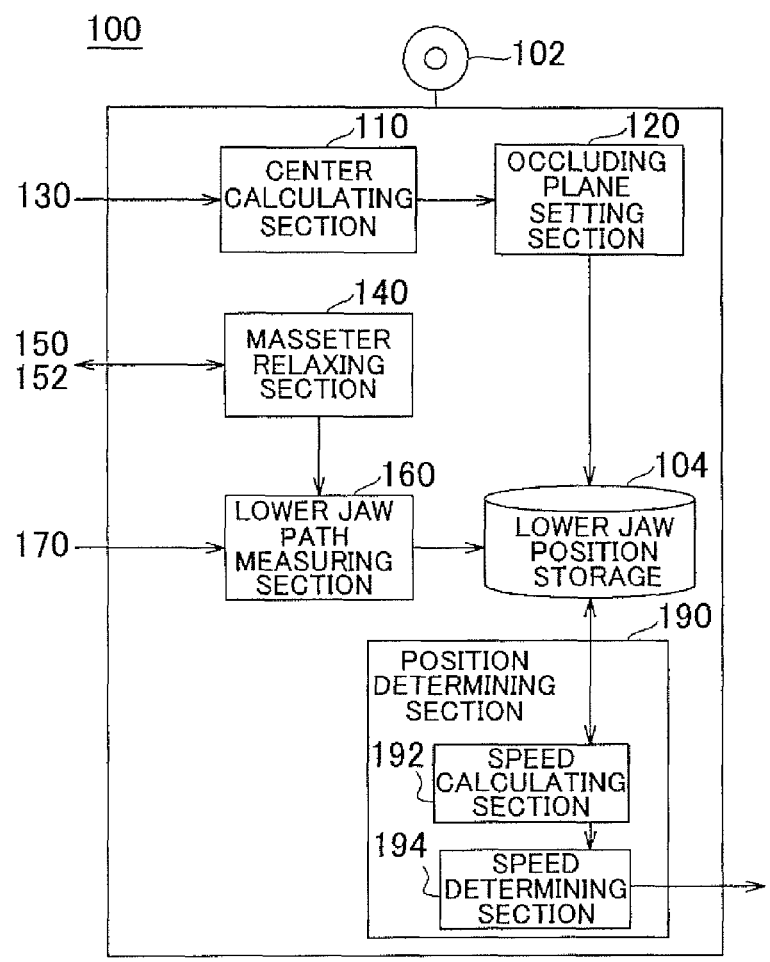
FIG. 7 is a functional block diagram showing a function of the lower jaw position determining apparatus 100.

FIG. 7 is a functional block diagram showing a function of the lower jaw position determining apparatus 100. The lower jaw position determining apparatus 100 shown in FIG. 7 includes a center calculating section 110, an occluding plane setting section 120, a masseter relaxing section 140, a lower jaw path measuring section 160, a position determining section 190, and a lower jaw position storage 104.

The center calculating section 110 obtains measurement data on the movement of the head 30, which has been measured by the head movement measuring section 130 while fixing the shoulders of the examinee 20 to the chair 24. Some examples of the movement of the head 30 include leaning forward, leaning backward, lateral leaning, and rotation of the head 30. Here, the posture of the examinee 20 affects the movement of the head 30 to a certain extent. In view of this, it is desirable to adjust the posture of the examinee 20 so that the movement of the head 30 can be measured under a condition that the head 30 is freely movable in anteroposterior directions, as well as left and right directions as much as possible. The measurement data is a three dimensional data showing the path of a plurality of dots with respect to the reference position 22, which may be represented by either a rectangular coordinate system or a spherical coordinate system.

Further, the center calculating section 110 calculates the center of movement 32 of the head 30 as three dimensional data with respect to the reference position 22, from the measurement data. In this case, the center calculating section 110 calculates the center of movement 32 by approximating the movement of the head 30 to the rotational movement of a rigid body. For example, the center calculating section 110 approximates the path of the magnetic sensor of the head movement measuring section 130 attached to the head 30 as an circular arc, and calculates the center of this circular arc, as the center of movement 32.

As seen in FIGS. 2-6, the head 30 moves with the spinal cord 34 as the center of movement 32. To be more specific, a human body is made such that bones and muscles including the atlas 38 and the axis 39 protect the spinal bone 34, for life support and for stably supporting the head 30. As shown in FIG. 6, the head 30 in its resting state is subjected to a load 50 of the barycenter of the lower jaw 40, a load 51 of the barycenter of a tong, a load 52 of the barycenter of the skull 36, and a load 54 of the barycenter of the brain within the skull 36. A drag 53 cancelling out these loads is exerted to a tangent point between the bilateral condylus occipitalis and the upper atlas joint surface as a point of action, and indirectly to the spinal code 34 as a point of action, which results in supporting the head 30. So as to ensure protection of the spinal code 34 even in the movement of the head 30, the head 30 moves with its center of movement 32 being the spinal code 34. For example, as shown in FIGS. 4-6, the upper joint surface of the atlas 38 is ovally shaped, with their foreheads corresponding to a part of the spherical surface 55 of an imaginary center 33, and the lowermost point of the spherical surface 55 corresponding to the center of movement 32. Note that the curved surface 56 is an imaginary spherical surface based on the curvature at the back of the atlas 38. When the skull 36 rotates, the skull 36 rotates with respect to the atlas 38, as well as the atlas 38 rotates with respect to the axis 39 around the vertical axis passing through the dens. As a result, the entire skull 36 rotates with respect to the center of movement 32 positioned in an area penetrated by the spinal cord 34. In addition, the center of curvature of the space of the median atlantoaxial joint between the joint surface of the dens of the axis 39 and the anterior arch joint surface of the atlas 38 passes through the spinal cord 34, and the tangent point between the lower joint surface of the atlas 38 and the upper joint surface of the axis passes through the spinal cord 34. Therefore, the skull 36 leans forward or backward with the center of the curvature as the center of movement 32. Furthermore, in the lateral leaning, the axis 39 leans relative to the third cervical vertebrae, and the skull 36 slides relative to the atlas 38, while no movement occurs in the atlantoaxial joint. As a result, the skull 36 laterally leans with its axis being the center of movement 32 positioned in the area passing through the spinal cord 34. This center calculating section 110 is able to calculate the center of movement 32 based on the above-mentioned measurement data, without directly obtaining the positions of the spinal cord 34 of the examinee 20 passing through the atlas 38 and the axis 39.

The occluding plane setting section 120 sets a horizontal plane passing through the center of movement 32 of the head 30, to be a normal occluding plane 44. Further, the occluding plane setting section 120 stores, in the lower jaw position storage 104, the set occluding plane 44 in association with the examinee ID identifying the examinee 20. The examinee ID is input from an input device, such as a keyboard, connected to the lower jaw position determining apparatus 100. Here, because the normal occluding plane 44 is a horizontal plane, in the rectangular coordinate system, it may take a one dimensional value in the height direction Z with respect to the reference position 22. FIG. 2 and FIG. 3 show one example of a current reference plane 45 of the examinee 20 and the normal occluding plane 44 set by the occluding plane setting section 120.

The masseter relaxing section 140 relaxes the masseter of the examinee 20. An example of the masseter relaxing section 140 is an apparatus generating a rectangular wave voltage pulse to the electrode pad 150. One example of the masseter relaxing section 140 is Myo-Monitor manufactured by Myotronics Inc., which emits a rectangular pulse having a voltage between 11V and 22V once every 1.5 seconds for a duration of 1.5 sec, with an electrode pad 150 attached to the left and right lower jaw notches of the examinee 20 as a negative pole, and an electrode pad 150 attached to the culmination of the back of the cervix of the examinee 20 as a positive pole. By doing so, the facial nerve directly below the negative pole and the trifacial nerve deeper inside are simultaneously stimulated, to cause the muscular substance under control of these nerves to involuntarily contract, thereby relaxing these muscular substances. Moreover, the masseter relaxing section 140 may use an electromyograph to measure to see whether the masseter is relaxed or not. Note that the masseter relaxing section 140 may be provided separately from the lower jaw position determinng apparatus 100 or may be integrally formed therewith.

When notified by the masseter relaxing section 140 that the masseter of the examinee 20 has been relaxed, the lower jaw path measuring section 160 measures the path of the masticatory movement from the rest position of the lower jaw 40 of the examinee 20 in that relaxed state to the occluding plane. Here, the lower jaw path measuring section 160 measures the path of the sensor 170 attached to the lower jaw 40 for each of a plurality of lower jaw positions of the examinee 20. The lower jaw path measuring section 160 stores, in the lower jaw position storage 104, measured data in association with each lower jaw position. Here, the sensor 170 is attached to a known position of the lower jaw 40. To be more specific, the sensor 170 is attached to the lower jaw 40 at the occluding plane 44, in a position having an attachment angle θ between a horizontal line and the straight line connecting between the center of movement 32 of the head 30 and the position of the sensor 170.

The position determining section 190 includes a speed calculating section 192 and a speed determining section 194. The speed calculating section 192 calculates a speed of the lower jaw for each lower jaw position, by referring to the data in the lower jaw position storage 104, and the speed determining section 194 extracts one of the lower jaw positions calculated by the speed calculating section 192, which has a speed satisfying a predetermined condition, and determines the extracted lower jaw position to be a normal lower jaw position. Accordingly, the position determining section 190, by referring to the data of the lower jaw position storage 104, finds, from among a plurality of lower jaw paths, a path whose center of movement, in approximating the masticatory movement of the lower jaw 40 to the rotational movement of a rigid body, matches the center of movement 32 of the head 30, and determines the lower jaw position corresponding to the found path to be a normal lower jaw position of the examinee 20, and outputs normal lower jaw position.

The following explains the reason why the normal jaw position for the examinee 20 is determined in a manner stated above. That is, as mentioned in explaining the center calculating section 110, the center of movement 32 of the head 30 should be the spinal cord 34. With this in view, even in movement of the lower jaw 40 during the masticatory movement, it is natural that a human body preferably moves the lower jaw 40 so that its center of movement matches the spinal cord 34, for the purpose of protecting the spinal cord 34 passing the atlas 38 and the axis 39 for life support and for stably supporting the head 30. The operation of the position determining section 190 is later described in greater details.

A recording medium 102 stores a program for realizing each function of the lower jaw position determining apparatus 100. The lower jaw position determining apparatus 100 may realize each operation by installing the program stored in the recording medium 102. Moreover, the lower jaw position determining apparatus 100 may obtain the program via a network such as the Internet.

FIG. 8 shows an example of information stored in the lower jaw position storage 104. The lower jaw position storage 104 shown in FIG. 8 stores, in association with an examinee ID, coordinates of a head center position calculated by the center calculating section 110.

Furthermore, the lower jaw position storage 104, also in association with this examinee identification information, stores a plurality of lower jaw positions. The lower jaw position storage 104 stores, as the lower jaw position, an amount of shift (mm) shifted in X (in the direction of left or right) and Y (in the direction of backward or forward) from the lower jaw position while the lower jaw is relaxed by the masseter relaxing section 140, as the point of origin. Furthermore, the lower jaw position storage 104, for each lower jaw position, a path of the sensor 170 measured by the lower jaw path measuring section 160 and a speed calculated by the position determining section 190 based on the path. Here, the lower jaw position storage 104 stores, as the path of the sensor 170, a position relative to the reference position 22 at a certain time interval, in association with the time interval. In the example of FIG. 8, the lower jaw position storage 104 stores the path and the speed directions α and β of the head 30 viewed in front and from the side. Note that in FIG. 8, for facilitating explanation, the path is shown by a line connecting the positions of the sensor 170 at the certain time interval. The lower jaw position storage 104 may store the data measured by the head movement measuring section 130.

Figure 9:
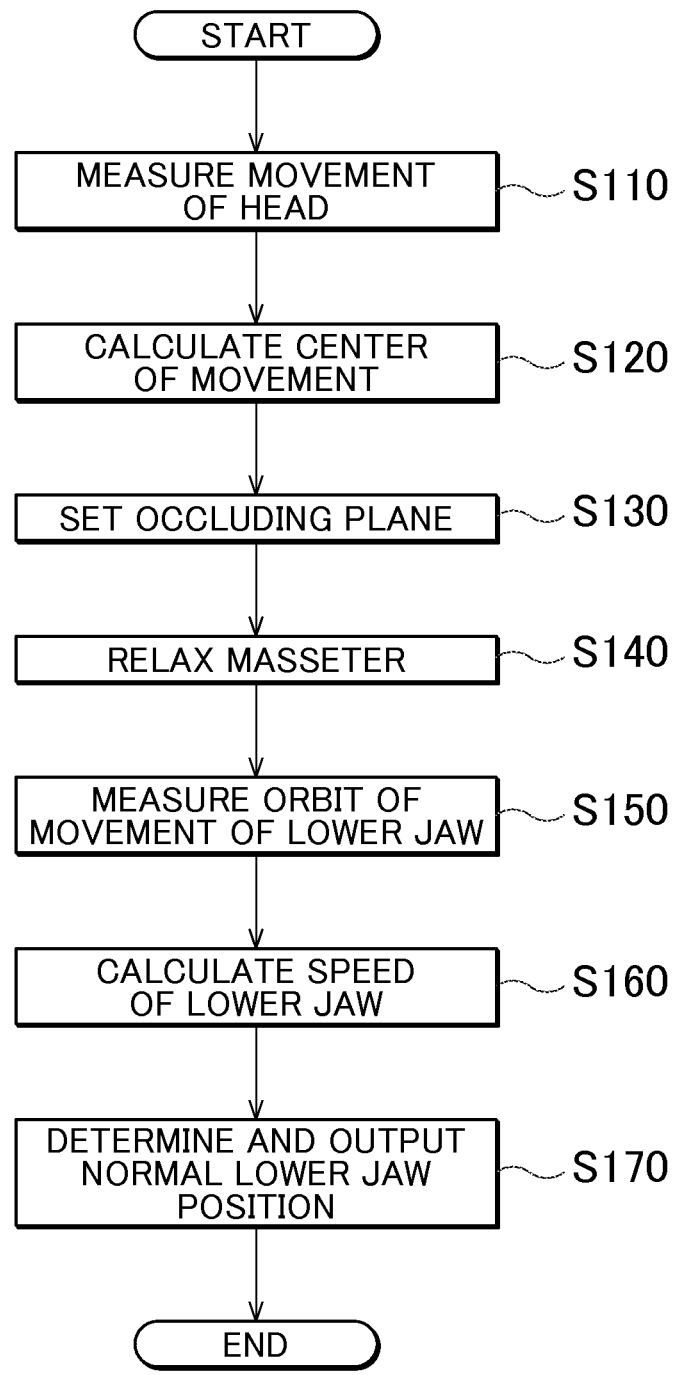
FIG. 9 is an exemplary flow chart showing an operation of the lower jaw position determining apparatus 100.

FIG. 9 is an exemplary flow chart showing an operation of the lower jaw position determining apparatus 100. The flowchart of FIG. 9 starts in response to reception of an input by the lower jaw position determining apparatus 100 via a keyboard or the like.

First, the head movement measuring section 130 measures (S110) the movement of the head 30 while the shoulders of the examinee 20 are fixed to the chair 24, and stores the measured data to the lower jaw position storage 104. Next, the center calculating section 110 obtains the measured data from the head movement measuring section 130, and calculates the center of movement 32 of the head 30 (S120). Further, the center calculating section 110 sets the horizontal plane passing through the center of movement 32 to be a normal occluding plane 44 (S130).

The masseter relaxing section 140 relaxes the masseter of the examinee 20 (S140). Further, the masseter relaxing section 140 notifies the lower jaw path measuring section 160 that the masseter of the examinee 20 has been relaxed (also in S140).

Upon reception of the notification from the masseter relaxing section 140, the lower jaw path measuring section 160 measures the path of the masticatory movement of the lower jaw 40 of the examinee 20 (S150). The lower jaw path measuring section 160 stores the measured data in the lower jaw position storage 104 (also in S150). Here, it is preferable to fix the head 30 of the examinee 20 to the chair 24 so that the straight line 47 connecting between the right eye and the left eye of the examinee 20 matches the horizontal line. This arrangement allows the path of the masticatory movement of the lower jaw 40 of the examinee 20 to be measured more accurately.

The speed calculating section 192, for obtaining the center of movement of the lower jaw 40 using the tangent method, calculates the speed of the sensor 170 when the lower jaw 40 reaches the occluding plane, from each of the plurality of paths by referring to the data of the lower jaw position storage 104, and stores the calculated speed in the lower jaw position storage 104 (S160). Here, the speed calculating section 192 may calculate the speed of the sensor 170 each time the lower jaw path measuring section 160 measures the path of a particular lower jaw position, or the speed calculating section 192 may calculate the speed at each lower jaw position after the lower jaw path measuring section 160 has measured the paths of the plurality of lower jaw positions.

For example, the speed calculating section 192, for a particular lower jaw position, for XZ direction positions of the sensor 170 at a certain time interval stored in the lower jaw position storage 104, by dividing the chronologically adjacent positions by the certain time interval, obtains the speed of the lower jaw 40 viewed in front as well as the speed direction a that is an angle between the speed and the vertical direction. Here, the speed calculating section 192 may calculate the speed direction a based on the difference between the position of the sensor 170 when the lower jaw 40 reaches the occluding plane 44 and the chronologically immediately preceding position of the sensor 170, or based on the average of the differences between the position of the sensor 170 when the lower jaw 40 reaches the occluding plane 44 and the position of the predetermined number of the chronologically preceding and adjacent positions thereof. Likewise, the speed calculating section 192, for a particular lower jaw position, for YZ direction positions of the sensor 170 at a certain time interval stored in the lower jaw position storage 104, by dividing the chronologically adjacent positions by the certain time interval, obtains the speed of the lower jaw 40 viewed from side as well as the speed direction β that is an angle between the speed and the vertical direction. Note that the occurrence of the lower jaw 40 reaching the occluding plane 44 can be known by detecting the event that the angle of the sensor 170 with respect to the horizontal plane with the center of movement 32 as its center has been equaled to the attachment angle θ.

The speed determining section 194 determines the normal lower jaw position for the examinee 20 based on the speed calculated by the speed calculating section 192, and displays the result to a display or the like (S170). Here, the speed determining section 194 extracts a lower jaw position having a smaller value of the speed direction α and a smaller difference between the speed direction β and the attachment angle θ. For the lower jaw position extracted in this way, since the speed direction α is small, the force exerted onto the lower jaw 40 at the occluding plane 44 is symmetrical with respect to left and right directions, and moreover since the speed direction β is substantially the same as the attachment angle θ, an upper vertical force is exerted onto the lower jaw 40 at the occluding plane 44. Accordingly, the lower jaw position corresponds to a lower jaw position whose center of movement, in approximating the masticatory movement of the lower jaw 40 to the rotational movement of a rigid body, has a path that matches the center of movement 32 of the head 30. Here, the speed determining section 194 may obtain the amount of shift in X in the left or right direction that causes the speed direction a to be zero, from a relation between the numerical value of the speed direction α and the amount of shift in X in the left or right direction of a lower jaw position, using extrapolation or interpolation. Likewise, the speed determining section 194 may obtain the amount of shift in Y in the backward or forward direction that causes the difference between speed direction β and the attachment angle θ to be zero, from a relation between the numerical value of the speed direction β and the amount of shift in Y in the forward or backward direction, using extrapolation or interpolation.

The above-described embodiment has explained a case where the lower jaw path measuring section 160 measures the path of one sensor 170. However, the number of sensors 170 is not limited to one. In another example, the lower jaw path measuring section 160 may detect the movement of a plurality of sensors provided at positions corresponding to three or more different positions, at least one of which differs at least in right or left direction, or forward or backward direction from each other with respect to the lower jaw 40 of the examinee 20 (e.g. apexes of a regular triangle). In Steps S160 and S170, the center of movement of the lower jaw 40 is obtained using a tangent method. However, a Reuleaux method may be used instead. In the Reuleaux method, the center of movement is approximated at the intersection of the bisector of two line segments measured in Step 150.

As described above, the present embodiment allows more accurate determination of a normal lower jaw position of the examinee 20. In particular, the lower jaw position that has a path whose center of movement, in approximating the masticatory movement of the lower jaw 40 to the rotational movement of a rigid body, matches the center of movement 32 of the head 30 is determined to be a normal lower jaw position of the examinee 20. Therefore, with the obtained lower jaw position, the examinee 20's posture is prevented from thrown off balance while adjusting the muscle power and the skeleton position to protect the center of the movement 32 (i.e. spinal chord 34) at the time of masticatory movement.

Figure 10:
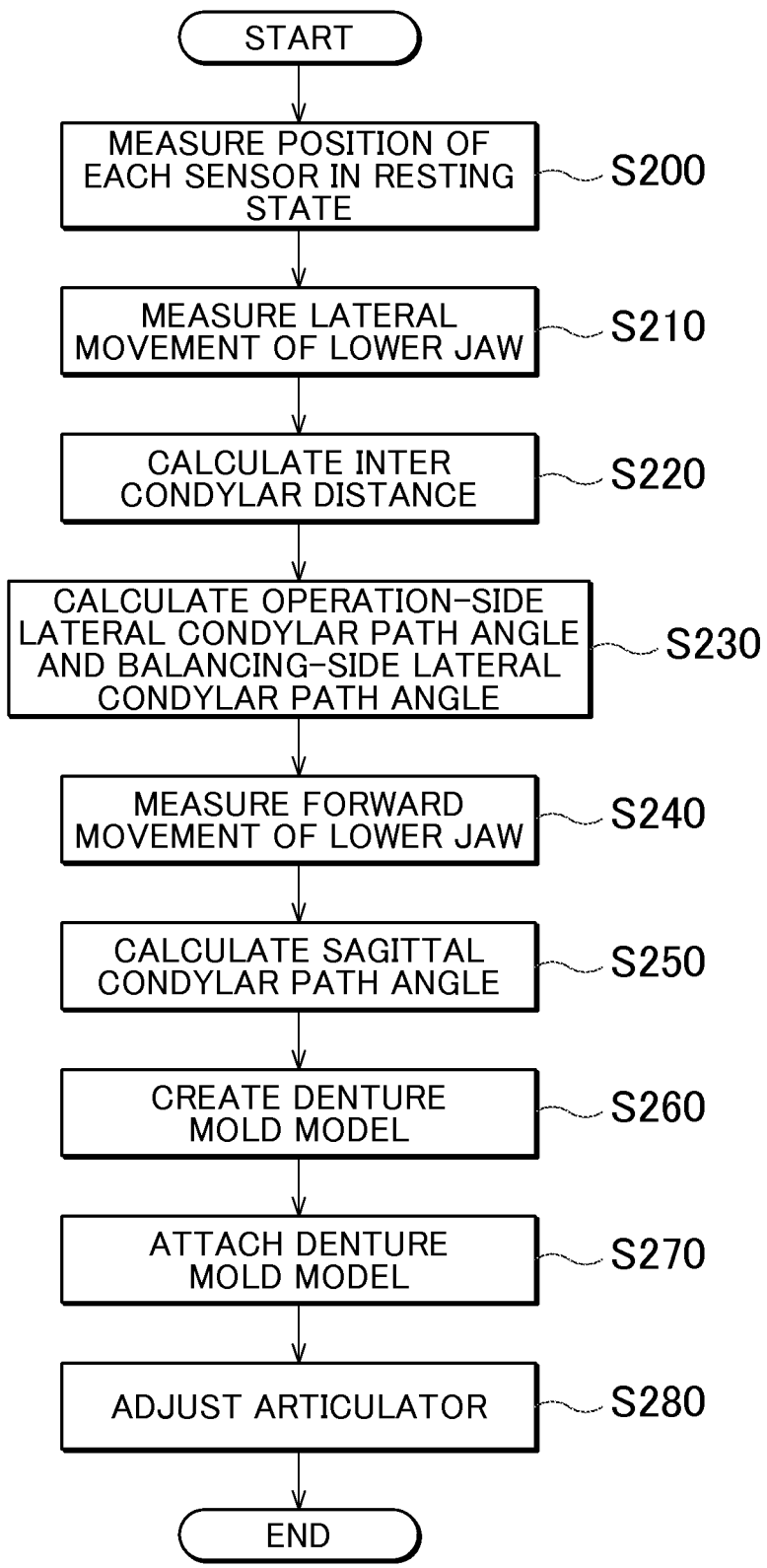
FIG. 10 is a flow chart showing an operation of another embodiment.

FIG. 10 is a flow chart showing an operation of another embodiment. The embodiment shown in FIG. 10 executes the operation of FIG. 10 in addition to the embodiment shown in FIG. 1 thorough FIG. 9.

In the operation of FIG. 10, the upper jaw and the lower jaw of the examinee 20 are provided with sensors 170, and the lower jaw path measuring section 160 measures the position of the sensors 170 (S200). Here, it is preferable that each of the upper jaw and the lower jaw be provided with a plurality of sensors 170. For example, each of the upper jaw and the lower jaw is provided with three sensors 170 which all together form an isosceles triangle. Here, the relative positions between the sensors 170 are measured with the upper jaw and the lower jaw in resting state at the respective jaw positions determined in Step S170 of FIG. 9.

Next, the head movement measuring section 130 of the lower jaw position determining system 10 measures the path of the lower jaw 40 having laterally moved by the examinee 20, starting from the lower jaw position determined in Step S170 of FIG. 9 (S210), and stores the measured data in the lower jaw position storage 104. Further, the position determining section 190 reads the data having been measured in Step S210 and stored in the lower jaw position storage 104, and calculates the position of the left and right condyles positions from the path of the lateral movement of the head 30, as well as the intercondylar distance which is the distance between the left and right condyles (S220). Moreover, the position determining section 190 calculates the operation-side lateral condylar path angle and the balancing-side lateral condylar path angle using the position of the left and right condyles and the mentioned lateral movement (S230). Here, the position determining section 190, for example, obtains the position of the instantaneous rotation center as the three dimensional position with respect to the sensor 170, using the path of the sensor 170 measured when the lower jaw 40 is laterally moved towards right from the lower jaw position determined in Step S170 and using the tangent method or the Reauleaux method explained above, and approximates the obtained position to be the right condyle position (S220). Likewise, the position determining section 190 sets the instantaneous rotation center resulting when the lower jaw 40 is laterally moved towards left from the lower jaw position calculated in Step S170 to be the left condyle position (S220). In addition, the distance between the left and right condyle positions is obtained (S220). Further, the position determining section 190 calculates the amount of movement of the left and right condyles in lateral movement, using the position of the left and right condyles obtained in Step S220 and the path of the lateral movement of the sensors 170, thereby calculating the operation-side lateral condylar path angle and the balancing-side lateral condylar path angle (S230).

Moreover, the head 30 measures the path of the lower jaw 40 moved forward by the examinee 20, from the lower jaw position of the examinee 20 determined in Step S170 explained above (S240), and stores the measured data in the lower jaw position storage 104. Further, the position determining section 190 reads the data having been measured in Step S240 and stored in the lower jaw position storage 104, and calculates the sagittal condylar path angle, from the path of the forward movement of the lower jaw 40 (S250). Here, the position determining section 190, for example, calculates the amount of shift of the left and right condyles in forward movement, from the positions of the left and right condyles obtained in Step S220 and the path of the forward movement of the sensors 170, thereby obtaining the sagittal condylar path angle (S250).

The position determining section 190 outputs the position of each sensor 170 measured in Step S200, the positions of the left and right condyles and the distance therebetween calculated in Step S220, the operation-side lateral condylar path angle and the balancing-side lateral condylar path angle calculated in Step S230, and the sagittal condylar path angle calculated in Step S250. Here, examples of the outputting performed by the position determining section 190 include displaying each numerical value on the display of the lower jaw position determining apparatus 100, and printing out the numerical value using a printer.

Here, it is also possible that a dentist or a dental practitioner take a denture mold of the examinee 20, to create a denture mold model (S260). Here, it is desirable that the position of each sensor attached to the upper jaw and the lower jaw of the examinee 20 in Step S200 be marked on the denture mold model.

The denture mold model is attached to the upper arch portion and the lower arch portion of the articulator (S270). Then the articulator is adjusted (S280). In this process, the articulator is first adjusted so that the relative positional relation of the sensors 170 outputted from the position determining section 190 matches the relative positional relation of the corresponding markings on the denture mold model attached to the articulartor. Next, the articulator is adjusted to realize therein the sagittal condylar path angle, the operation-side lateral condylar path angle and the balancing-side lateral condylar path angle, and the distance between the left and right condyles, which have been outputted from the position determining section 190.

As described above, the method of FIG. 10 allows accurate numerical calculation of the sagittal condylar path angle, the operation-side lateral condylar path angle and the balancing-side lateral condylar path angle, and the distance between the left and right condyles. Moreover, the sagittal condylar path angle, the operation-side lateral condylar path angle and the balancing-side lateral condylar path angle, and the distance between the left and right condyles are realized on an articulator without any need to use complicated apparatuses such as a face bow liable to cause human errors.

Figure 11:
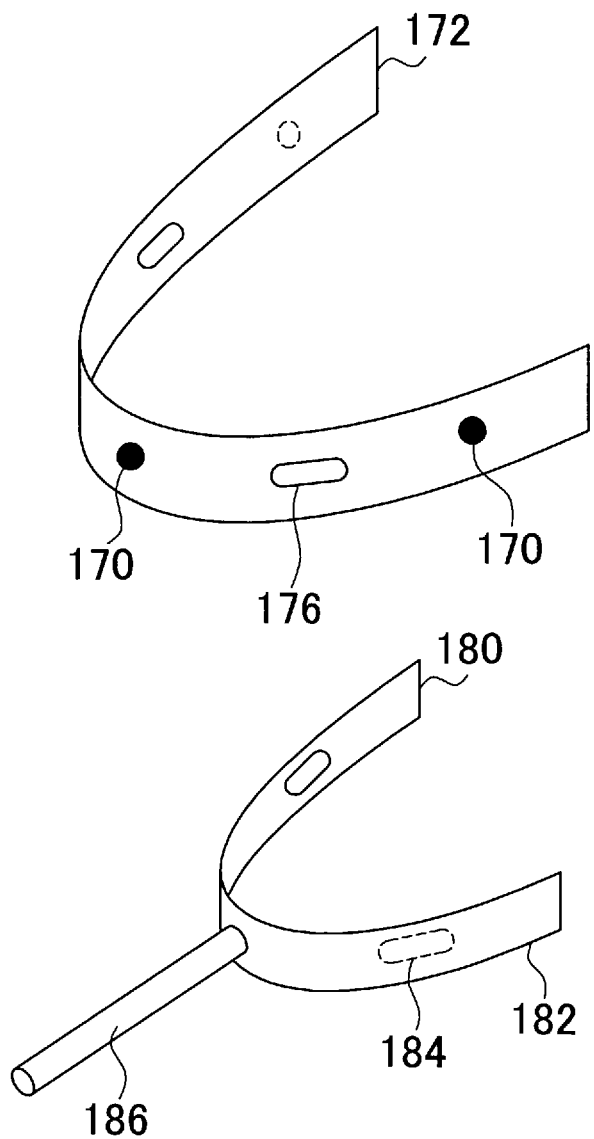
FIG. 11 is a perspective view showing an overview of a sensor unit 162 that includes sensors 170.

FIG. 11 is a perspective view showing an overview of a sensor unit 162 that includes sensors 170. The sensor unit 162 in this drawing includes a sensor body 172 shaped as a plate bent in U-shape, three sensors 170 arranged on the sensor body 172 at positions forming an isosceles triangle, and two engaging sections 176 arranged among the three sensors 170 on the sensor body 172. Further, the sensor unit 162 includes an attachment tool 180 easily attached/removed with respect to the sensor body 172. The attachment tool 180 includes a tool body 182 in bent U-shape corresponding to the curve of the sensor body 174, two engaging sections 184 arranged on the tool body 182 in positions corresponding to the two engaging sections 176, and an elongating section 186 that outwardly extends from the convex side of the U-shaped portion of the tool body 182.

In the described configuration, one of the engaging section 176 and the engaging section 184, corresponding to each other, is convex and the other is concave, so as to fit each other. Accordingly, the sensor body 174 on which the sensors 170 are arranged is supported by the attachment tool 180.

Figure 12:
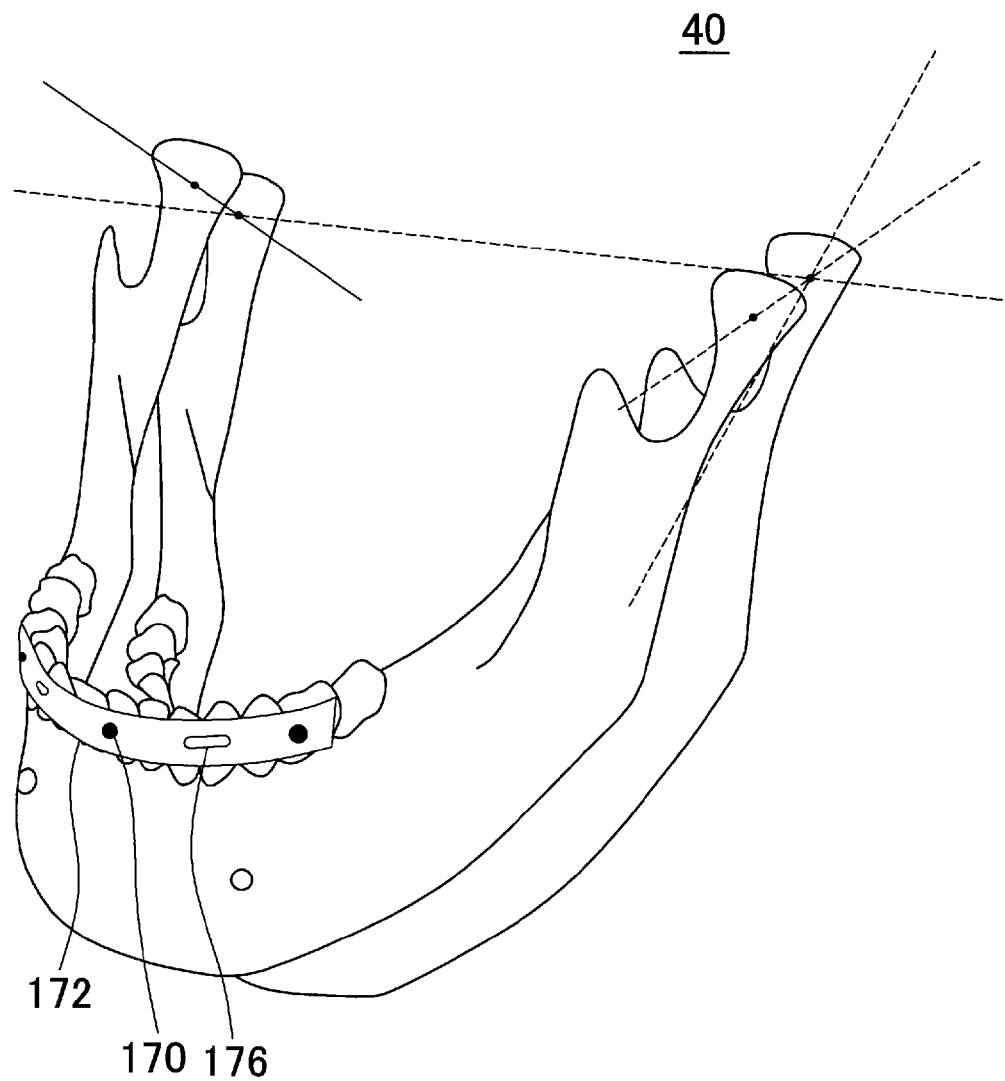
FIG. 12 is a perspective view showing a state in which the sensors 170 are attached to the lower jaw 40.

FIG. 12 is a perspective view showing a state in which the sensors 170 of the sensor unit 162 shown in FIG. 11 are attached to the lower jaw 40. Note that although this drawing shows only the sensors 170 attached to the lower jaw 40, sensors 170 having the same configuration are also attached to the upper jaw 40.

Figure 14:
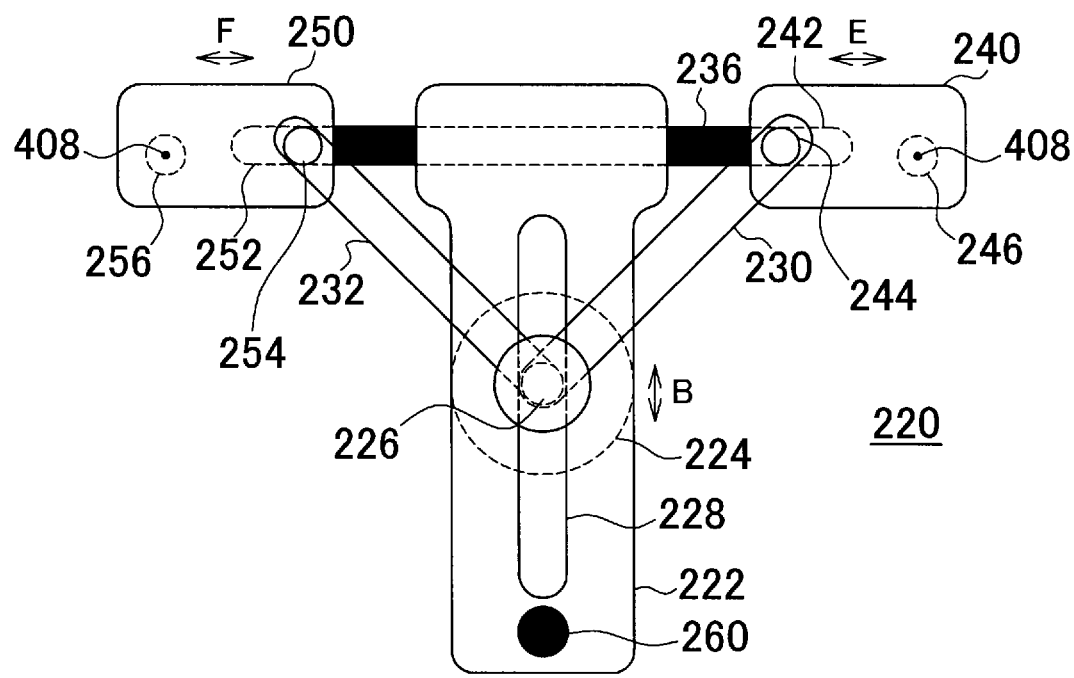
FIG. 14 is a plan view of an upper arch portion 220.
Figure 15:
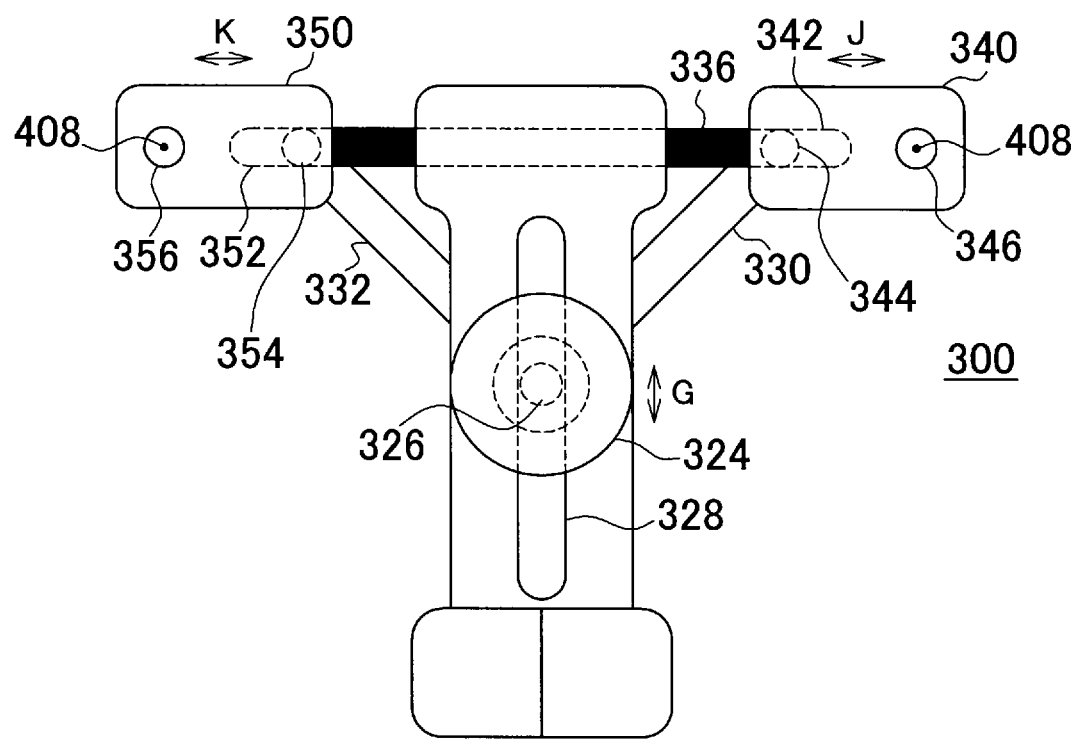
FIG. 15 is a plan view of a lower arch portion 300.

FIG. 13 is a side view of an example of an articulator 200 used in Step S270 and Step S280 in FIG. 10. FIG. 14 is a plan view of an upper arch portion 220, and FIG. 15 is a plan view of a lower arch portion 300. This articulator 200 accurately makes an accurate replica of the distance between the left and right condyles of the exmaminee 20.

The articulator 200 includes an upper arch portion 220 and a lower arch portion 300. An occluding plane setting section 120 is attached to the upper arch portion 220, and a lower denture mold model 212 is attached to the lower arch portion 300. The upper arch portion 220 rotates in the direction of the arrow A of FIG. 13, with respect to the lower arch portion 300.

As shown in FIG. 14, the upper arch portion 220 includes an upper arch body 222 extending in an anteroposterior direction (in the up and down direction in FIG. 14), an arm 236 penetrating the upper arch body 222 in the horizontal direction, connectors 240, 250 respectively provided at both ends of the arm 236, an incisal pin 260 provided at the anterior edge of the upper arch body 222, and a leg 234 provided downward from the upper arch body 222. The upper arch body 222 is further provided with a groove 228 elongating in the anteroposterior direction, and a link pin 226 is slidably inserted to the groove 228 in the direction of the arrow B of FIG. 14. A model attaching section 224 supporting the upper denture mold model 210 is attached to the link pin 226. The link pin 226 is rotatably inserted to a through hole provided at an end of a pair of link members 230, 232. The other end of the pair of link members 230, 232 is also provided with a through hole, to which link pins 244, 254 protruding upward from the connectors 240, 250 are rotatably inserted. A concave portion 242 is provided on a side surface of the connector 240, in which an end of the arm 236 is slidably accommodated. The connector 240 also includes a spherical bearing 246 rotatably abutting against a sphere 346 of the lower arch portion 300.

Likewise, the connector 250 includes a concave portion 252 and a spherical bearing 256. Although not illustrated in the drawings, known means for restricting the amount of rotation of the spherical bearing 246 and the spherical bearing 256 may be provided to adjust the sagittal condylar path angle, and the operation-side lateral condylar path angle and the balancing-side lateral condylar path angle of the articulator 200.

As shown in FIG. 15, the lower arch portion 300 includes a lower arch body 322 extending in an anteroposterior direction (in the up and down direction in FIG. 15), an arm 336 penetrating the lower arch body 322 in the horizontal direction, upright portions 340, 350 provided at both ends of the arm 336, and a leg 334 provided downward from the lower arch body 322. The lower arch body 322 is further provided with a groove 328 elongating in the anteroposterior direction, and a link pin 326 is slidably inserted to the groove 328 in the direction of the arrow G of FIG. 15. A model attaching section 324 supporting the lower denture mold model 212 is attached to the link pin 326. The link pin 326 is rotatably inserted to a through hole provided at an end of a pair of link members 330, 332. The other end of the pair of link members 330, 332 is also provided with a through hole, to which link pins 344, 354 protruding downward from the upright portions 340, 350 are rotatably inserted.

The upright portion 340 stands upright in the up and down direction, the upper surface of which is provided with the sphere 346. A concave portion 342 is provided in a lower part of a side surface of the upright portion 340, in which an end of the arm 336 is slidably accommodated. The upright portion 350 also includes a concave portion 352 and the sphere 346.

In the stated configuration, the upper arch portion 220 is provided above the lower arch portion 300, and the spherical bearing 246 is supported by the sphere 346, and the spherical bearing 256 is supported by the sphere 356. As a result, the upper arch portion 220 is rotatably supported with respect to the center of the spheres 346 and 356 of the lower arch portion 300, as shown in FIG. 13.

Here, the respective centers of the spheres 346 and 356 correspond to the left and right condyles positions 408. According to the above-stated configuration, the connectors 240 and 250 are slidable in the directions of the arrows E and F with respect to the arm 236, and the upright portions 340 and 350 are slidable in the directions of the arrows J and K with respect to the arm 336. As a result, the distance between the left and right condyles of the examinee 20 can be accurately copied. Furthermore, since the connectors 240, 250, and the model attaching section 224 are mutually linked via the link members 230 and 232, the movement of any one of them will also move the other two, and that the connectors 240 and 250 can be moved in the same distance as each other. Note that an alternative arrangement is also possible in which the connectors 240, 250 and the model attaching section 224 are movable independent from each other, instead of providing the link members 230 and 232. Likewise, since the upright portions 340, 350, and the model attaching section 324 are mutually linked via the link members 330 and 332, the movement of any one of them will also move the other two, and that the upright portions 340 and 350 can be moved in the same distance as each other. Note that an alternative arrangement is also possible in which the upright portions 340 and 350 and the model attaching section 324 are movable independent from each other, instead of providing the link members 330 and 332.

Figure 16:
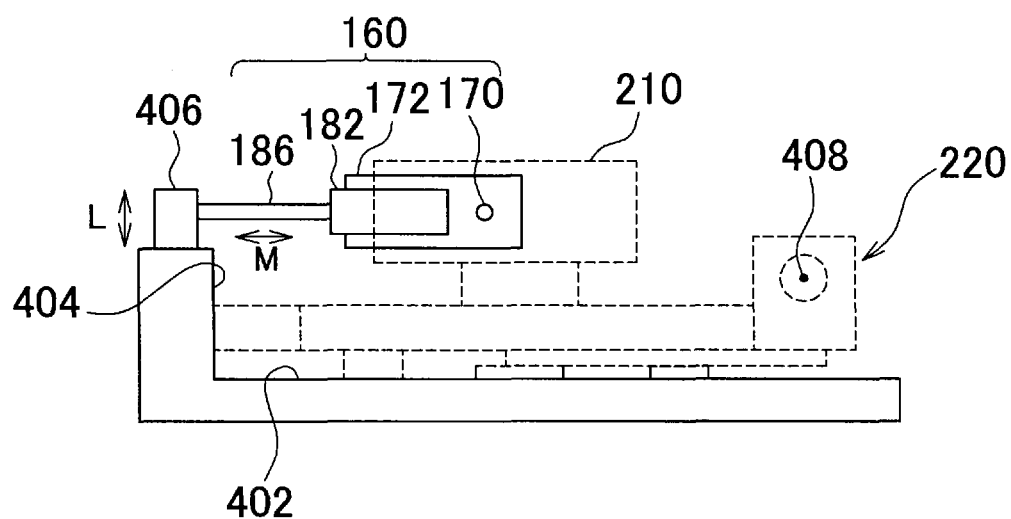
FIG. 16 is a side view of a pedestal 400 for mounting an upper denture mold model 210.

FIG. 16 is a side view of a pedestal 400 for mounting an upper denture mold model 210. The pedestal 400 has a reference bottom surface 402 and a reference anterior surface 404 against which the reference bottom surface 402 abuts at its forehead. An upper arch portion 220 or a lower arch portion 300 is mounted on the reference bottom surface 402. Furthermore, the pedestal 400 includes an up-and-down section 406 in the vicinity of the reference anterior surface 404, which moves up and down with respect to the reference bottom surface 402. The up-and-down section 406 slidably and removably holds the elongating section 186 of the lower jaw path measuring section 160, in the horizontal direction (in the direction of the arrow M in FIG. 16).

When attaching the upper denture mold model 210 to the upper arch portion 220, the upper arch portion 220, in the orientation that is vertically reverse to the orientation in actual usage (see FIG. 13), is first placed on the reference bottom surface 402, as in FIG. 16. In this process, the anterior surface of the upper arch portion 220 is made to abut against the reference anterior surface 404. As a result, the position of the upper arch portion 220 (especially the condyle position 408) is aligned with the pedestal 400.

While keeping the upper denture mold model 210 created in Step S260 of FIG. 10 attached to the lower law path measuring section 160, the elongating section 186 of the sensor unit 162 is inserted to the up-and-down section 406. By adjusting the height of the up-and-down section 406 and the anteroposterior positioning of the elongating section 186, the positional relation between the condyle position calculated in Step S220 of FIG. 10 and the sensor 170 is copied to the positional relation between the condyle position 408 of the upper arch portion 220 mounted on the pedestal 400 and the sensor 170. After the mentioned positional relation is realized, the upper denture mold model 210 is attached to the model attaching section 224, using plaster or the like. Here, a detector such as a magnet can be provided to the condyle position 408, while providing the pedestal 400 with a measuring section for measuring the position of the detector. By doing so, the measurement section can be used to measure the three dimensional position of the condyle position 408 and the three dimensional position the sensor 170 of the sensor unit, while adjusting the height of the up-and-down section 406 as well as the anteroposterior positioning of the elongating section 186 to realize the positional relation between the condyle position calculated in Step S220 of FIG. 10 and the sensor 170.

Figure 17:
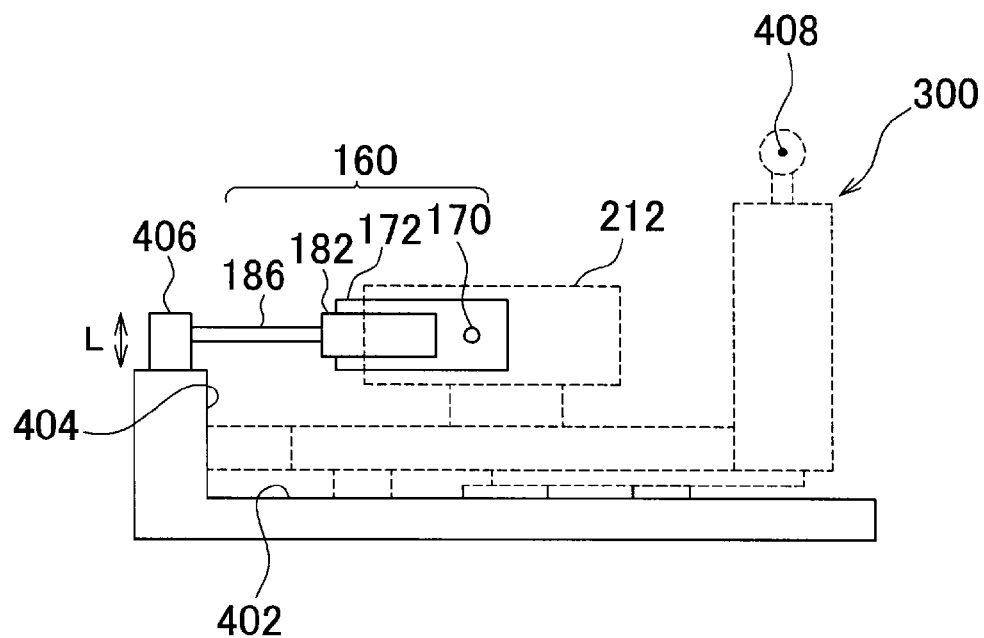
FIG. 17 is a side view of the pedestal 400 for mounting a lower denture mold model 212.

FIG. 17 is a side view of the pedestal 400 for mounting a lower denture mold model 212. In the case of the lower denture mold model 212, just as in the case of the upper denture mold model 210, by adjusting the height of the up-and-down section 406 and the anteroposterior positioning of the elongating section 186, the positional relation between the condyle position calculated in Step S220 of FIG. 10 and the sensor 170 is copied to the positional relation between the condyle position 408 of the lower arch portion 300 mounted on the pedestal 400 and the sensor 170. After the mentioned positional relation is realized, the lower denture mold model 212 is attached to the model attaching section 324, using plaster or the like.

The upper arch portion 220 with the upper denture mold model 210 attached thereon is mounted, with its face down, to the lower arch portion 300 with the lower denture mold model 212 attached thereon. As a result, the three dimensional relation of the normal position of both of the upper and lower jaws of the examinee 20 is copied onto the articulator 200. Furthermore, known means for restricting the amount of rotation of the spherical bearing 246 and the spherical bearing 256 helps copy, onto the articulator 200, the sagittal condylar path angle, and the operation-side lateral condylar path angle and the balancing-side lateral condylar path angle calculated in Steps S230 and S250.

As described above, the embodiment shown in FIGS. 13-17 allows to copy, on the articulator 200, the three dimensional positional relation of the correct jaw position of the upper and lower jaws of the examinee 20, without using an occlusal registration material such as wax which tends to cause human and chronological errors and operational troubles.

The operations, the processes, the steps, or the like in the apparatus, the system, the program, and the method described in the claims, the specification, and the drawings are not necessarily performed in the described order. The operations, the processes, the steps, or the like can be performed in an arbitrary order, unless the output of the former-described processing is used in the later processing. Even when expressions such as "First," or "Next," or the like are used to explain the operational flow in the claims, the specification, or the drawings, they are intended to facilitate the understanding of the invention, and are never intended to show that the described order is mandatory.

What is claimed is:

1. A lower jaw position determining system for determining a normal lower jaw position of an examinee, comprising:
    a computer;
    a head movement measuring section for measuring movement of the head using a sensor configured to be fixed to a head of the examinee;
    a center calculating section for obtaining measurement data based on the movement of the head measured by the head movement measuring section, and calculating, using the computer, an approximate center of movement resulting from approximating the movement of the head as rotational movement of a rigid body;
    a lower jaw path measuring section for measuring a plurality of paths of masticatory movement of the lower jaw using a sensor configured to be attached to the lower jaw of the examinee, for a plurality of lower jaw positions of the examinee; and
    a position determining section for (i) approximating, using the computer, the masticatory movement of the lower jaw as rotational movement of a rigid body to find one of the plurality of measured paths of the lower jaw whose center of movement in the approximation matches the calculated approximate center of movement of the head, (ii) determining, using the computer, an approximate lower jaw position that corresponds to the found path of the lower jaw, and (iii) outputting the determined approximate lower jaw position as a normal lower jaw position for the examinee.

2. The lower jaw position determining system according to claim 1, further comprising a masseter relaxing section for relaxing a masseter of the examinee, wherein
    the lower jaw path measuring section is operable to measure a path of masticatory movement of the lower jaw for each of the plurality of lower jaw positions from a resting position of the relaxed masseter of the examinee to an occluding plane.

3. The lower jaw position determining apparatus according to claim 1, wherein
    the lower jaw measuring section measures the plurality of paths while the head of the examinee is fixed in a posture such that a straight line connecting between a right eye and a left eye of the examinee matches a horizontal line.

4. The lower jaw position determining apparatus according to claim 1, further comprising an occluding plane setting section for setting a horizontal line passing through the calculated approximate center of movement to be a normal occluding plane, wherein
    the position determining section includes:
        a speed calculating section for calculating speeds of the sensor configured to be attached to the lower jaw of the examinee when the lower jaw reaches the occluding plane, from the plurality of measured paths; and
        a speed determining section for obtaining one of the calculated speeds that has a smaller horizontal component, and that has an angle with respect to a vertical line equal to an angle formed between (i) a straight line connecting the center of movement of the head and a position of the sensor configured to be attached to the lower jaw of the examinee and (ii) a horizontal line, and
    the position determining section is operable to output the lower jaw position for which the speed is obtained as the normal lower jaw position of the examinee.

5. The lower jaw position determining apparatus according to claim 4, wherein
    the sensor configured to be attached to the lower jaw of the examinee is one of a plurality of sensors provided for the lower jaw of the examinee in three or more positions different from each other in at least forward, backward, left, and right directions, and
    the lower jaw path measuring section measures the plurality of paths using the plurality of sensors.

6. The lower jaw position determining apparatus according to claim 1, wherein
    the head movement measuring section measures a path of the lower jaw laterally moved by the examinee from the determined approximate lower jaw position;
    the position determining section calculates an operation-side lateral condylar path angle and a balancing-side lateral condylar path angle, from the measured path of the lower jaw laterally moved;
    the head movement measuring section measures a path of the lower jaw moved forward by the examinee from the determined approximate lower jaw position; and
    the position determining section calculates a sagittal condylar path angle from the measured path of the jaw moved forward, wherein
    the position determining section is operable to output the calculated operation-side lateral condylar path angle, the calculated balancing-side lateral condylar path angle, and the calculated sagittal condylar path angle.

7. The lower jaw position determining apparatus according to claim 6, wherein
    the position determining section is operable to calculate a distance between right and left condyles, based on the measured path of the lower jaw moved forward and the measured path of the lower jaw laterally moved, and output the distance.

8. The lower jaw position determining apparatus according to claim 1, wherein
    the position determining section is operable to output an amount of shift from a lower jaw position where the examinee is relaxed.

9. A computer program product having computer instructions, recorded on a non-transitory computer readable medium, for enabling a computer executing the computer instructions to perform operations comprising:
    obtaining measurement data by measuring movement of a head of an examinee, and calculating an approximate center of movement resulting from approximating the movement of the head as rotational movement of a rigid body;
    measuring a plurality of paths of masticatory movement of the lower jaw, for a plurality of lower jaw positions of the examinee;
    approximating the masticatory movement of the lower jaw as rotational movement of a rigid body to find one of the plurality of measured paths of the lower jaw whose center of movement in the approximation matches the calculated approximate center of movement of the head;
    determining an approximate lower jaw position that corresponds to the found path of the lower jaw; and
    outputting the determined approximate lower jaw position as a normal lower jaw position for the examinee.

10. The computer program product according to claim 9, wherein a computer executing the computer instructions is enabled to perform operations further comprising:
    relaxing a masseter of the examinee, wherein
    the operation of measuring a plurality of paths includes measuring a path of masticatory movement of the lower jaw for each of the plurality of lower jaw positions from a resting position of the relaxed masseter of the examinee to an occluding plane.

11. The computer program product according to claim 9, wherein a computer executing the computer instructions is enabled to perform operations further comprising:
    fixing the head of the examinee in a posture such that a straight line connecting between a right eye and a left eye of the examinee matches a horizontal line.

12. The computer program product according to claim 9, wherein a computer executing the computer instructions is enabled to perform operations further comprising:
    setting a horizontal line passing through the calculated approximate center of movement to be a normal occluding plane, wherein
    the operation of measuring a plurality of paths includes measuring the plurality of paths by detecting movement of one or more magnetic members attached to one or more known positions of the lower jaw of the examinee,
    the operation of determining an approximate lower jaw position includes:
        calculating speeds of the one or more magnetic members when the lower jaw reaches the occluding plane, from the plurality of measured paths; and
        obtaining one of the calculated speeds that has a smaller horizontal component, and that has an angle with respect to a vertical line equal to an angle formed between (i) a straight line connecting the center of movement of the head and a position of one of the one or more magnetic members and (ii) a horizontal line, and
    the operation of outputting the determined approximate lower jaw position includes outputting the lower jaw position for which the speed is obtained as the normal lower jaw position of the examinee.

13. The computer program product according to claim 12, wherein
    the operation of measuring a plurality of paths includes measuring the plurality of paths by detecting movement of one or more magnetic members provided for the lower jaw of the examinee in three or more positions different from each other in at least forward, backward, left, and right directions.

14. The computer program product according to claim 9, wherein a computer executing the computer instructions is enabled to perform operations further comprising:

measuring a path of the lower jaw laterally moved by the examinee from the determined approximate lower jaw position;

calculating an operation-side lateral condylar path angle and a balancing-side lateral condylar path angle, from the measured path of the lower jaw laterally moved;

measuring a path of the lower jaw moved forward by the examinee from the determined approximate lower jaw position; and calculating a sagittal condylar path angle from the measured path of the jaw moved forward, wherein the operation of outputting the determined approximate lower jaw position includes outputting the calculated operation-side lateral condylar path angle, the calculated balancing-side lateral condylar path angle, and the calculated sagittal condylar path angle.

15. The computer program product according to claim 14, wherein a computer executing the computer instructions is enabled to perform operations further comprising:

calculating a distance between right and left condyles, based on the measured path of the lower jaw moved forward and the measured path of the lower jaw laterally moved, wherein the operation of outputting the determined approximate lower jaw position includes outputting the distance.

16. The computer program product according to claim 9, wherein the operation of outputting the determined approximate lower jaw position includes outputting an amount of shift from a lower jaw position where the examinee is relaxed.

* * * * *